(12) United States Patent
Dakka et al.

(10) Patent No.: US 8,791,306 B2
(45) Date of Patent: *Jul. 29, 2014

(54) OXIDATION OF ALKYLAROMATIC COMPOUNDS

(71) Applicant: ExxonMobil Chemical Patents Inc., Baytown, TX (US)

(72) Inventors: Jihad M. Dakka, Whitehouse Station, NJ (US); Stephen Zushma, Clinton, NJ (US); Jon E. R. Stanat, Westhampton Beach, NY (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/903,675

(22) Filed: May 28, 2013

(65) Prior Publication Data

US 2013/0274524 A1   Oct. 17, 2013

Related U.S. Application Data

(62) Division of application No. 13/122,608, filed as application No. PCT/US2009/057239 on Sep. 17, 2009, now Pat. No. 8,461,398.

(60) Provisional application No. 61/122,452, filed on Dec. 15, 2008.

(51) Int. Cl.
| | |
|---|---|
| *C07C 409/00* | (2006.01) |
| *C07C 45/53* | (2006.01) |
| *C07C 37/08* | (2006.01) |
| *C07C 409/08* | (2006.01) |
| *C07C 409/14* | (2006.01) |
| *C07D 209/48* | (2006.01) |
| *C07C 409/10* | (2006.01) |
| *C07C 407/00* | (2006.01) |
| *B01J 31/02* | (2006.01) |

(52) U.S. Cl.
CPC ........... *C07C 407/00* (2013.01); *C07C 2101/14* (2013.01); *C07C 45/53* (2013.01); *C07C 37/08* (2013.01); *C07C 409/08* (2013.01); *C07C 409/14* (2013.01); *B01J 31/0247* (2013.01); *C07D 209/48* (2013.01); *C07C 409/10* (2013.01); *B01J 2231/70* (2013.01)
USPC ........... 568/573; 568/558; 568/568; 568/569; 568/570

(58) Field of Classification Search
CPC .......................... C07C 409/16; C07C 409/00
USPC .................... 568/558, 568, 569, 573
See application file for complete search history.

(56) References Cited

U.S. PATENT DOCUMENTS

| | | | |
|---|---|---|---|
| 2,584,103 | A | 2/1952 | Pines et al. |
| 3,418,256 | A | 12/1968 | Rigney et al. |
| 3,819,735 | A | 6/1974 | Argento et al. |
| 3,959,381 | A | 5/1976 | Arkell et al. |
| 4,051,191 | A | 9/1977 | Ward |
| 4,136,123 | A | 1/1979 | Hutchings |
| 4,255,592 | A | 3/1981 | Kawai et al. |
| 4,282,383 | A | 8/1981 | Dai et al. |
| 4,450,303 | A | 5/1984 | Drake |
| 4,490,565 | A | 12/1984 | Chang et al. |
| 4,490,566 | A | 12/1984 | Chang et al. |
| 4,891,458 | A | 1/1990 | Innes et al. |
| 4,992,606 | A | 2/1991 | Kushnerick et al. |
| 5,030,739 | A | 7/1991 | Foricher et al. |
| 5,059,736 | A | 10/1991 | Tamura et al. |
| 5,081,323 | A | 1/1992 | Innes et al. |
| 5,166,454 | A | 11/1992 | Harandi et al. |
| 5,177,283 | A | 1/1993 | Ward |
| 5,183,945 | A | 2/1993 | Stibrany et al. |
| 5,298,667 | A | 3/1994 | Iwanaga et al. |
| 5,304,684 | A | 4/1994 | Nishida et al. |
| 5,334,774 | A | 8/1994 | Kogure et al. |
| 5,336,820 | A | 8/1994 | Owen et al. |
| 5,371,310 | A | 12/1994 | Bennett et al. |
| 5,405,814 | A | 4/1995 | Beech, Jr. et al. |
| 5,557,024 | A | 9/1996 | Cheng et al. |
| 5,922,920 | A | 7/1999 | Bond et al. |
| 5,981,420 | A | 11/1999 | Nakano et al. |

(Continued)

FOREIGN PATENT DOCUMENTS

| | | |
|---|---|---|
| EP | 0 824 962 | 2/1998 |
| EP | 0 858 835 | 8/1998 |

(Continued)

OTHER PUBLICATIONS

Arends et al, Tetrahedron, 2002, 58, pp. 9055-9061.*
K. Hattori et al., "*Kinetics Of Liquid Phase Oxidation Of Cumene In Bubble Column*", Journal Of Chemical Engineering of Japan, 1970, vol. 3, No. 1, pp. 72-78.
Y. Isakov et al. "*Catalytic Properties Of Palladium-Zeolite Systems In The Synthesis Of Sec-Butylbenzene From Benzene And Ethylene*", Inst. Org. Khim, im. N. D. Zelinskogo, Moscow, Russia, Neftekhimiya, 1994, vol. 34, No. 2, pp. 151-170.

(Continued)

*Primary Examiner* — Sudhakar Katakam
(74) *Attorney, Agent, or Firm* — Jaime L. Sullivan; Siwen Chen

(57) ABSTRACT

In a process for oxidizing an alkylaromatic compound to the corresponding hydroperoxide, a feed comprising an alkylaromatic compound is contacted with an oxygen-containing gas in the presence of a catalyst comprising a cyclic imide. The contacting is conducted at a temperature of about 90° C. to about 150° C., with the cyclic imide being present in an amount between about 0.05 wt % and about 5 wt % of the alkylaromatic compound in the feed and the catalyst being substantially free of alkali metal compounds. The contacting oxidizes at least part of the alkylaromatic compound in said feed to the corresponding hydroperoxide.

16 Claims, 5 Drawing Sheets

(56) References Cited

U.S. PATENT DOCUMENTS

| | | | |
|---|---|---|---|
| 6,002,057 | A | 12/1999 | Hendriksen et al. |
| 6,051,521 | A | 4/2000 | Cheng et al. |
| 6,169,215 | B1 | 1/2001 | Levin et al. |
| 6,169,216 | B1 | 1/2001 | Levin et al. |
| 6,291,718 | B1 | 9/2001 | Matsui et al. |
| 6,297,406 | B1 | 10/2001 | Levin et al. |
| 6,410,804 | B1 | 6/2002 | Levin et al. |
| 6,440,886 | B1 | 8/2002 | Gajda et al. |
| 6,476,276 | B2 | 11/2002 | Matsui et al. |
| 6,528,658 | B1 | 3/2003 | Miura et al. |
| 6,720,462 | B2 | 4/2004 | Kuhnle et al. |
| 6,852,893 | B2 | 2/2005 | Kuhnle et al. |
| 7,038,089 | B2 | 5/2006 | De Frutos Escrig et al. |
| 7,282,613 | B2 | 10/2007 | Black et al. |
| 7,326,815 | B2 | 2/2008 | Dakka et al. |
| 7,799,956 | B2 | 9/2010 | Cheng et al. |
| 8,461,398 | B2 * | 6/2013 | Dakka et al. .......... 568/573 |
| 2002/0026680 | A1 | 3/2002 | Kingry et al. |
| 2002/0169331 | A1 | 11/2002 | Miura et al. |
| 2003/0083527 | A1 | 5/2003 | Kuhnle et al. |
| 2004/0014985 | A1 | 1/2004 | Sugahara |
| 2004/0162448 | A1 | 8/2004 | Yang et al. |
| 2004/0236152 | A1 | 11/2004 | Black et al. |
| 2005/0043559 | A1 | 2/2005 | Marhold et al. |
| 2005/0065381 | A1 | 3/2005 | DeFrutos Escrig et al. |
| 2005/0167658 | A1 | 8/2005 | Williams et al. |
| 2007/0167658 | A1 | 7/2007 | Onuma et al. |
| 2007/0265476 | A1 * | 11/2007 | Dakka et al. .......... 568/385 |
| 2008/0086018 | A1 | 4/2008 | Cheng et al. |
| 2008/0269507 | A1 | 10/2008 | Kajikawa et al. |
| 2010/0222609 | A1 | 9/2010 | Dakka et al. |

FOREIGN PATENT DOCUMENTS

| | | |
|---|---|---|
| EP | 1 074 536 | 2/2001 |
| EP | 1 088 807 | 4/2001 |
| FR | 2 182 802 | 12/1973 |
| JP | 62-114922 | 5/1987 |
| JP | 11-180913 | 7/1999 |
| JP | 2001-192354 | 7/2001 |
| JP | 2002-282698 | 10/2002 |
| JP | 2003-034679 | 2/2003 |
| JP | 2004-035460 | 2/2004 |
| JP | 2004-247897 | 9/2004 |
| RU | 417405 | 8/1974 |
| RU | 265349 | 10/1976 |
| RU | 1245564 | 6/1982 |
| WO | 94/20213 | 9/1994 |
| WO | 99/47485 | 9/1999 |
| WO | 1 088 809 | 4/2001 |
| WO | 2006/015826 | 2/2006 |
| WO | 2008/037435 | 4/2008 |
| WO | 2009/025939 | 2/2009 |
| WO | 2010/098916 | 9/2010 |

OTHER PUBLICATIONS

Y. Isakov et al., "*Study Of Polyfunctional Zeolite Catalysts. Communication 2. Formation Of A Catalyst For Synthesis Of Sec-Butylbenzene Prepared From Nickel Acetylacetonate And Cay Zeolite*", Inst. Org. Khim. im. Zelinskogo, Moscow, USSR, 1976, vol. 3, pp. 498-504.

Y. Ishii et al., "*A Novel Catalysis Of N-Hydroxyphthalimide In The Oxidation Of Organic Substrates By Molecular Oxygen*", Journal of Organic Chemistry, 1995, vol. 60, pp. 3934-3935.

Y. Ishii, "*Recent Progress In Aerobic Oxidation Of Hydrocarbons By N-Hydroxyimides*", Catalysis Today, 2006, vol. 117, pp. 105-113.

K. Minachey et al., "*Alkylation Of Benzene By Ethylene On Catalysts Produced From Synthetic Zeolites Ultrasil*", Inst. Org. Khim, im. Zelinskogo, Moscow, USSR, Neftekhimiya, 1988, vol. 28, No. 2, pp. 151-158.

K. Minachey et al., "*Bifunctional Catalysts For The Alkylation Of Aromatic Compounds By Ethylene*", USSR, Lektsii-Vses, Shk. Katal, 1981, vol. 2, pp. 76-111.

K. Minachey et al., "*Study Of The Nature Of Bifunctional Catalysts For The Synthesis Of Sec-Butylbenzene From Ethylene And Benzene*", Inst. Org. Khim, im. Zelinskogo, Moscow, USSR, Geterog. Katal., 1979, 4$^{th}$ Ed., Pt. 2, pp. 485-492.

K. Ohkubo et al., "*A Kinetic Study on the Homogeneous Liquid-phase Oxidation of Cumene in the Presence of Triphenylsulfonium Chloride*", Bulletin of the Chemical Society of Japan, 1969, vol. 42, No. 7, pp. 1800-1806.

A. Sachanen et al., "*High-Temperature Alkylation of Aromatic Hydrocarbons*", Industrial and Engineering Chemistry, 1941, vol. 33, No. 12, pp. 1540-1544.

R. Sheldon et al., "*Organocatalytic Oxidations Mediated By Nitroxyl Radicals*", Adv. Synth. Catal., 2004, vol. 346, pp. 1051-1071.

V. Sidorov et al., "*Alkylation Of Benzene With Olefins*", Sernaya Kislota Protsessakh Neftekhim, 1975, pp. 172-177.

M. Weber, "*Large Bubble Columns For The Oxidation Of Cumene In Phenol Processes*", Chem. Eng. Technol., 2002, vol. 25, No. 5, pp. 553-558.

Y. Yen, "*Phenol*", Process Economics Report No. 22B, Stanford Research Institute, 1977, pp. 113-421 and 261-263.

Burghardt et al., "*Studies On Oxidation Of Sec-Butylbenzene To The Hydroperoxide*", Chemia Stosowana, XXIII, 1979, vol. 4, pp. 443-457.

J. Howard et al., "*Absolute Rate Constants for Hydrocarbon Oxidation. XI. The Reactions of Tertiary Peroxy Radicals*[1,2]", Canadian Journal of Chemistry, 1968, vol. 46, pp. 2656-2660.

J. Howard et al., "*Absolute Rate Constants for Hydrocarbon Oxidation. VIII. The Reactions of Cumylperoxy Radicals*[1]", Canadian Journal of Chemistry, 1968, vol. 46, pp. 1018-1022.

J. Howard, "*Absolute Rate Constants for Hydrocarbon Autoxidation. XXII. The Autoxidation of Some Vinyl Compounds*[1]", Canadian Journal of Chemistry, 1972, vol. 50, pp. 2298-2304.

J. Howard et al., "*Absolute Rate Constants for Hydrocarbon Autoxidation. XV. The Induced Decomposition of Some T-Hydroperoxides*[1]", Canadian Journal of Chemistry, 1969, vol. 47, pp. 3797-3801.

J. Howard et al., "*Absolute Rate Constants for Hydrocarbon Autoxidation. XIV. Termination Rate Constants for Tertiary Peroxy Radicals*[1]", Canadian Journal of Chemistry, 1969, vol. 47, pp. 3793-3795.

T. Iwahama et al., "*Aerobic Oxidation of Alcohols to Carbonyl Compounds Catalyzed by N-Hydroxyphthalimide (NHPI) Combined with Co (acac)$_3$* ", Tetrahedron Letters, 1995, vol. 36, No. 38, pp. 6923-6926.

J. Kochi, "*Chemistry of Alkoxy Radicals: Cleavage Reactions*", Journal of the American Chemical Society, 1962, vol. 84, pp. 1193-1197.

Sakaguchi et al., "*Oxidation of Organic Substrates with Molecular Oxygen Catalyzed by Vanadomolybdophosphate (NPV$_6$Mo$_6$) Combined with N-Hydroxyphthalimide (NHPI)*", Technology Reports of Kansai University, 1996, No. 38, pp. 123-131.

Weissermel et al., "*10. Components for Polyamides*", Industrial Organic Chemistry, 3$^{rd}$ Edition, 1997, D-69451, p. 251-262.

Arends et al. (Tetrahedron, 2002, 58, pp. 9055-9061).

\* cited by examiner

US 8,791,306 B2
OXIDATION OF ALKYLAROMATIC COMPOUNDS

PRIORITY CLAIM

This application is a divisional of and claims priority and benefit of U.S. application Ser. No. 13/122,608, filed Apr. 5, 2011 (now allowed); International Application No. PCT/US2009/057239, filed Sep. 17, 2009 and U.S. Provisional Application Ser. No. 61/122,452, filed Dec. 15, 2008, the disclosures of which are hereby incorporated by reference in their entireties.

FIELD

The present invention relates to a process for oxidizing alkylaromatic compounds and for converting the oxidation product to phenol and the corresponding ketone.

BACKGROUND

Phenol is an important product in the chemical industry and is useful in, for example, the production of phenolic resins, bisphenol A, ε-caprolactam, adipic acid, and plasticizers.

Currently, the most common route for the production of phenol is the Hock process. This is a three-step process in which the first step involves alkylation of benzene with propylene to produce cumene, followed by oxidation of the cumene to the corresponding hydroperoxide and then cleavage of the hydroperoxide to produce equimolar amounts of phenol and acetone. However, the world demand for phenol is growing more rapidly than that for acetone. In addition, the cost of propylene relative to that of butenes is likely to increase, due to a developing shortage of propylene.

Thus, a process that uses butenes or higher alkenes instead of propylene as feed and coproduces methyl ethyl ketone (MEK) or higher ketones, such as cyclohexanone, rather than acetone may be an attractive alternative route to the production of phenols. For example, there is a growing market for MEK, which is useful as a lacquer, a solvent and for dewaxing of lubricating oils. In addition, cyclohexanone is used as an industrial solvent, as an activator in oxidation reactions and in the production of adipic acid, cyclohexanone resins, cyclohexanone oxime, caprolactam and nylon 6.

It is known that phenol and MEK can be produced from sec-butylbenzene, in a process where sec-butylbenzene is oxidized to obtain sec-butylbenzene hydroperoxide and the peroxide decomposed to the desired phenol and methyl ethyl ketone. An overview of such a process is described in pages 113-121 and 261-263 of Process Economics Report No. 22B entitled "Phenol", published by the Stanford Research Institute in December 1977.

For example, in our International Patent Publication No. WO06/015826, we have described a process for producing phenol and methyl ethyl ketone, in which benzene is contacted with a $C_4$ alkylating agent under alkylation conditions with a catalyst comprising zeolite beta or a molecular sieve having an X-ray diffraction pattern including d-spacing maxima at 12.4±0.25, 6.9±0.15, 3.57±0.07 and 3.42±0.07 Angstrom to produce an alkylation effluent comprising sec-butylbenzene. The sec-butylbenzene is then oxidized to produce a hydroperoxide and the hydroperoxide is decomposed to produce phenol and methyl ethyl ketone. The oxidation step can be conducted with or without a catalyst under conditions including a temperature between about 70° C. and about 200° C., such as about 90° C. to about 130° C., and a pressure of about 0.5 to about 10 atmospheres (50 to 1000 kPa). Suitable catalysts are said to include the N-hydroxy substituted cyclic imides described in Published U.S. Patent Application No. 2003/0083527.

There is a need to find an oxidation process for sec-butylbenzene and cyclohexylbenzene that is highly selective to sec-butylbenzene or cyclohexylbenzene hydroperoxide, that is less sensitive to the presence of impurities than the existing oxidation processes, and that allows efficient commercial scale production of phenol and MEK or phenol and cyclohexanone.

It is known from, for example, U.S. Pat. Nos. 6,852,893 and 6,720,462 that certain cyclic imides, such as N-hydroxyphthalimide, in combination with free radical initiators, such as peroxy compounds or azo compounds, are effective catalysts in the catalytic oxidation of a wide variety of aliphatic or aromatic hydrocarbons, including alkyl aromatic hydrocarbons, such as cumene, cyclohexylbenzene, cyclododecylbenzene and sec-butylbenzene, to the corresponding hydroperoxides. The patents teach that the oxidation can be conducted over a wide range of process conditions including a temperature of 0 to 500° C. and a molar ratio of the catalyst to the hydrocarbon to be oxidized between $10^{-6}$ mol % and 10 mol %. However, no suggestion is provided in either patent as to the efficacy, or the preferred conditions, of the process for the selective oxidation of sec-butylbenzene to sec-butylbenzene hydroperoxide or cyclohexylbenzene to cyclohexylbenzene hydroperoxide.

U.S. Pat. No. 7,038,089 discloses a process for preparing hydroperoxides from their corresponding hydrocarbons which comprises oxidizing the hydrocarbons, particularly ethylbenzene, at a temperature in the range between 130 and 160° C. with an oxygen containing gas in the presence of a catalyst comprising a cyclic imide compound and an alkali metal compound. In particular, the '089 patent teaches that when oxidation of ethylbenzene is carried out in the presence of a catalytic comprising a cyclic imide and an alkaline metal compound, simultaneously high reaction rate and high selectivity to the corresponding hydroperoxide are obtained, superior to those which are obtained when both components from the catalytic system are used independently. In contrast, according to the '089 patent, when the cyclic imide alone is used as the catalyst, high imide concentrations have to be avoided for cost and product impurity reasons, but reducing the imide concentration to tolerable levels, requires a rise in temperature to increase reaction rate, leading to a decrease of the selectivity to hydroperoxide to unacceptable levels.

According to the present invention, it has now been found that, with sec-butylbenzene and cyclohexylbenzene, oxidation can be conducted at commercially viable conversion rates and sec-butylbenzene and cyclohexylbenzene hydroperoxide selectivities in the presence of a cyclic imide catalyst, without the addition of alkaline metal compound, provided the conversion is conducted over a relatively narrow range of temperature and cyclic imide concentration. Contrary to the teaching in U.S. Pat. No. 7,038,089, with sec-butylbenzene oxidation and cyclohexylbenzene, it has been found that the presence of an alkaline metal compound significantly reduces the activity and hydroperoxide selectivity of the oxidation catalyst.

SUMMARY

In one aspect, the present invention resides in a process for oxidizing an alkylaromatic compound to the corresponding alkylaromatic hydroperoxide, the process comprising contacting an alkylaromatic compound of general formula (I):

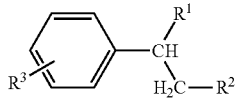

(I)

in which $R^1$ and $R^2$ each independently represents hydrogen or an alkyl group having from 1 to 4 carbon atoms, provided that $R^1$ and $R^2$ may be joined to form a cyclic group having from 4 to 10 carbon atoms, said cyclic group being optionally substituted, and $R^3$ represents hydrogen, one or more alkyl groups having from 1 to 4 carbon atoms or a cyclohexyl group, with oxygen in the presence of a catalyst comprising a cyclic imide of the general formula (II):

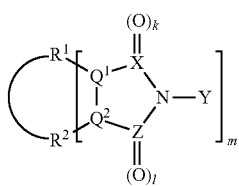

(II)

wherein each of $R^1$ and $R^2$ is independently selected from hydrocarbyl and substituted hydrocarbyl radicals having 1 to 20 carbon atoms, or from the groups $SO_3H$, $NH_2$, OH, and $NO_2$ or from the atoms H, F, Cl, Br, and I, provided that $R^1$ and $R^2$ can be linked to one another via a covalent bond;
each of $Q^1$ and $Q^2$ is independently selected from C, CH, $CR^3$;
each of X and Z is independently selected from C, S, $CH_2$, N, P and elements of Group 4 of the Periodic Table;
Y is O or OH;
k is 0, 1, or 2;
l is 0, 1, or 2;
m is 1 to 3; and
$R^3$ can be any of the entities listed for $R^1$; and
wherein said contacting is conducted at a temperature of about 90° C. to about 150° C., said cyclic imide is present in an amount between about 0.05 wt % and about 5 wt % of the alkylaromatic in said feed, and said catalyst is substantially free of alkali metal compounds, said contacting oxidizing at least part of the alkylaromatic in said feed to the corresponding alkylaromatic hydroperoxide.

Conveniently, said cyclic imide obeys the general formula (III):

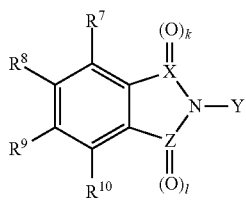

(III)

wherein each of $R^7$, $R^8$, $R^9$, and $R^{10}$ is independently selected from hydrocarbyl and substituted hydrocarbyl radicals having 1 to 20 carbon atoms, or from the groups $SO_3H$, $NH_2$, OH and $NO_2$, or from the atoms H, F, Cl, Br and I;
each of X and Z is independently selected from C, S, $CH_2$, N, P and elements of Group 4 of the Periodic Table;
Y is O or OH;
k is 0, 1, or 2; and
l is 0, 1, or 2.

Conveniently, said alkylaromatic compound of general formula (I) is selected from ethylbenzene, cumene, sec-butylbenzene, p-methyl-sec-butylbenzene, 1,4-diphenylcyclohexane, sec-pentylbenzene, sec-hexylbenzene, cyclopentylbenzene, cyclohexylbenzene and cyclooctylbenzene, with sec-butylbenzene and cyclohexylbenzene being preferred.

Conveniently, said contacting is conducted at a temperature of between about 120° C. and about 150° C., such as between about 125° C. and about 140° C., and at a pressure between about 15 kPa and about 500 kPa, such as between 15 kPa to about 150 kPa.

Conveniently, said cyclic imide is present in an amount between about 0.05 wt % and about 5 wt % of the alkylaromatic in said feed during said contacting.

Conveniently, said contacting converts at least 4 wt % per hour of said alkylaromatic with a selectivity to the corresponding alkylaromatic hydroperoxide of at least 90 wt %.

In one embodiment the process of the invention further comprises converting the hydroperoxide into a phenol and an aldehyde or ketone of the general formula $R^1COCH_2R^2$ (IV) in which $R^1$ and $R^2$ have the same meaning as in formula (I).

DETAILED DESCRIPTION OF THE EMBODIMENTS

Figure 1:
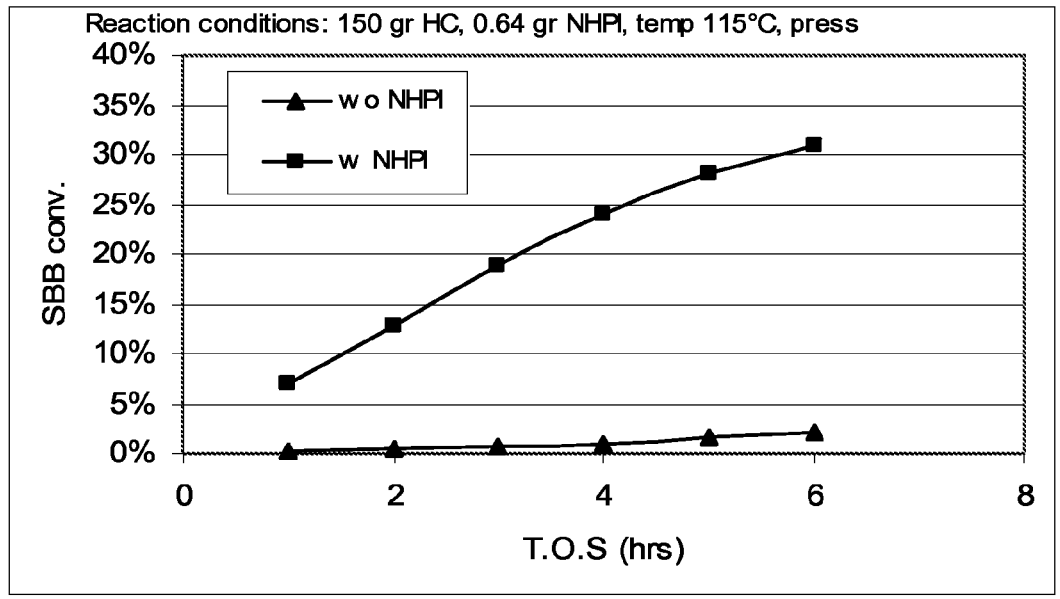
FIG. 1 is a graph plotting sec-butylbenzene conversion against time on stream (T.O.S) in the oxidation of sec-butylbenzene at 115° C. without N-hydroxyphthalimide (NHPI) according to the process of Example 1 and in the presence of 0.43 wt % NHPI according to the process of Example 2.

The terms "group", "radical", and "substituent" are used interchangeably in this document. For purposes of this disclosure, "hydrocarbyl radical" is defined to be a radical, which contains hydrogen atoms and up to 20 carbon atoms and which may be linear, branched, or cyclic, and when cyclic, aromatic or non-aromatic. "Substituted hydrocarbyl radicals" are radicals in which at least one hydrogen atom in a hydrocarbyl radical has been substituted with at least one functional group or where at least one non-hydrocarbon atom or group has been inserted within the hydrocarbyl radical.

As used herein, the new numbering scheme for the Periodic Table Groups is employed as disclosed in Chemical and Engineering News, 63(5), 27 (1985).

Described herein is a process for oxidizing an alkylaromatic to the corresponding hydroperoxide and optionally for cleaving the resultant hydroperoxide produced in (a) to produce phenol and the corresponding ketone. The oxidation process comprises contacting a feed comprising an alkylaromatic compound to the corresponding alkylaraomtic hydroperoxide, the process comprising contacting an alkylaromatic compound of general formula (I):

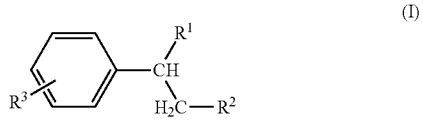

(I)

in which $R^1$ and $R^2$ each independently represents hydrogen or an alkyl group having from 1 to 4 carbon atoms, provided that $R^1$ and $R^2$ may be joined to form a cyclic group having from 4 to 10 carbon atoms, said cyclic group being optionally substituted, and $R^3$ represents hydrogen, one or more alkyl groups having from 1 to 4 carbon atoms or a cyclohexyl group, with oxygen in the presence of a catalyst comprising a cyclic imide of the general formula (II):

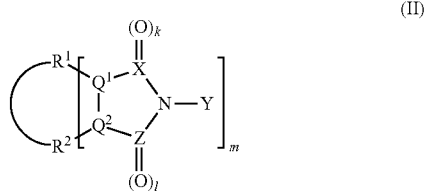

(II)

wherein each of $R^1$ and $R^2$ is independently selected from hydrocarbyl and substituted hydrocarbyl radicals having 1 to 20 carbon atoms, or the groups $SO_3H$, $NH_2$, OH and $NO_2$, or the atoms H, F, Cl, Br and I, provided that $R^1$ and $R^2$ can be linked to one another via a covalent bond; each of $Q^1$ and $Q^2$ is independently selected from C, CH, $CR^3$; each of X and Z is independently selected from C, S, $CH_2$, N, P and elements of Group 4 of the Periodic Table; Y is O or OH; k is 0, 1, or 2; 1 is 0, 1, or 2; m is 1 to 3; and $R^3$ can be any of the entities (radicals, groups, or atoms) listed for $R^1$. The oxidation is conducted at a temperature of about 90° C. to about 150° C., with the cyclic imide being present in an amount between about 0.05 wt % and about 5 wt % of the alkylaromatic in the feed and the catalyst being substantially free of alkali metal compounds.

The phrase "provided that $R^1$ and $R^2$ may be joined" and so on is used herein to mean that, as an alternative to each of $R^1$ and $R^2$ being a ("monovalent") alkyl group, the two "alkyl" entities designated "$R^1$" and "$R^2$" are joined into a ("divalent") hydrocarbyl chain (having 2 to 8 carbons in that chain), with respective ends of that "divalent" chain begin linked to the C atoms specifically shown in formula (I) to form a ring. Thus, in an embodiment, $R^1$ and $R^2$ together constitute a hydrocarbyl moiety that connects to the carbon atoms of formula (I) form a cyclic group having from 4 to 10 carbon atoms, conveniently a cyclohexyl group, which may be substituted with one or more alkyl group having from 1 to 4 carbon atoms or with one or more phenyl groups. Examples of suitable alkylaromatic compounds are ethylbenzene, cumene, sec-butylbenzene, p-methyl-sec-butylbenzene, 1,4-diphenylcyclohexane, sec-pentylbenzene, sec-hexylbenzene, cyclopentylbenzene, cyclohexylbenzene and cyclooctylbenzene, with sec-butylbenzene and cyclohexylbenzene being preferred. It will also be understood that in the case where $R^1$ and $R^2$ are joined to form a cyclic group, the number of carbons forming the cyclic ring is from 4 to 10. However, that ring may itself carry one or more substituents, such as one or more alkyl groups having from 1 to 4 carbon atoms or one or more phenyl groups, as in the case of 1,4-diphenylcyclohexane.

Sec-butylbenzene Production

In one embodiment, the alkylaromatic compound may be sec-butylbenzene which may be produced by alkylating benzene with at least one $C_4$ alkylating agent under alkylation conditions in the presence of a heterogeneous catalyst. The alkylation conditions conveniently include a temperature of from about 60° C. to about 260° C., for example between about 100° C. and about 200° C. The alkylation pressure is conveniently 7000 kPa or less, for example from about 1000 to about 3500 kPa. The alkylation is conveniently carried out at a weight hourly space velocity (WHSV) based on $C_4$ alkylating agent of between about 0.1 and about 50 $hr^{-1}$, for example between about 1 and about 10 $hr^{-1}$.

The $C_4$ alkylating agent conveniently comprises at least one linear butene, namely butene-1, butene-2 or a mixture thereof. The alkylating agent can also be an olefinic $C_4$ hydrocarbon mixture containing linear butenes, such as can be obtained by steam cracking of ethane, propane, butane, LPG and light naphthas, catalytic cracking of naphthas and other refinery feedstocks and by conversion of oxygenates, such as methanol, to lower olefins. For example, the following $C_4$ hydrocarbon mixtures are generally available in any refinery employing steam cracking to produce olefins and are suitable for use as the $C_4$ alkylating agent: a crude steam cracked butene stream, Raffinate-1 (the product remaining after solvent extraction or hydrogenation to remove butadiene from the crude steam cracked butene stream) and Raffinate-2 (the product remaining after removal of butadiene and isobutene from the crude steam cracked butene stream).

Cyclohexylbenzene Production

In a further practical embodiment, the alkylaromatic compound of general formula (I) is cyclohexylbenzene and is preferably produced by contacting benzene with hydrogen in the presence of a heterogeneous bifunctional catalyst which comprises at least one metal having hydrogenation activity, typically selected from the group consisting of palladium, ruthenium, nickel and cobalt, and a crystalline inorganic oxide material having alkylation activity, typically at least one molecular sieve of the MCM-22 family (as defined below). The contacting step is conveniently conducted at a temperature of about 50° C. to about 350° C. and/or a pressure of about 100 to about 7000 kPa and/or a benzene to hydrogen molar ratio of about 0.01 to about 100 and/or a WHSV of about 0.01 to about 100.

In the case where the alkylaromatic compound that is oxidized according to the invention is cyclohexylbenzene, the oxidation product is cyclohexylbenzene hydroperoxide and the cleavage product comprises phenol and cyclohexanone. The crude cyclohexanone and crude phenol from the cleavage step may be subjected to further purification to produce purified cyclohexanone and phenol. A suitable purification process includes, but is not limited to, a series of distillation towers to separate the cyclohexanone and phenol from other species. The crude or purified cyclohexanone may itself be subjected to dehydrogenation in order to convert it to phenol. Such dehydrogenation may be performed, for example, over a catalyst such as platinum, nickel or palladium.

The alkylation catalyst is conveniently zeolite beta, which is describe din detail in U.S. Pat. No. 3,308,069, or more preferably is at least one molecular sieve of the MCM-22 family. As used herein, the term "MCM-22 family material" (or "material of the MCM-22 family" or "molecular sieve of the MCM-22 family" or "MCM-22 family zeolite"), includes one or more of:

molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference);

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of the MCM-22 family include those molecular sieves having an X-ray diffraction pattern including d-spacing maxima at 12.4±0.25, 6.9±0.15, 3.57±0.07 and 3.42±0.07 Angstrom. The X-ray diffraction data used to characterize the material are obtained by standard techniques such as using the K-alpha doublet of copper as incident radiation and a diffractometer equipped with a scintillation counter and associated computer as the collection system.

Materials of the MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), UZM-8 (described in U.S. Pat. No. 6,756,030), and mixtures thereof.

Molecular sieves of the MCM-22 family are preferred as the alkylation catalyst since they have been found to be highly selective to the production of sec-butylbenzene, as compared with the other butylbenzene isomers. Preferably, the molecular sieve is selected from (a) MCM-49, (b) MCM-56 and (c) isotypes of MCM-49 and MCM-56, such as ITQ-2.

Oxidation Process

The oxidation step in the present process is accomplished by contacting a feed comprising an alkylaromatic compound such as sec-butylbenzene and cyclohexylbenzene with an oxygen-containing gas in the presence of a catalyst comprising a cyclic imide of the general formula (II):

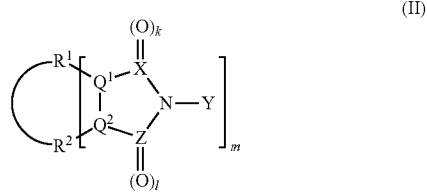

(II)

wherein each of $R^1$ and $R^2$ is independently selected from hydrocarbyl and substituted hydrocarbyl radicals having 1 to 20 carbon atoms, or the groups $SO_3H$, $NH_2$, OH and $NO_2$, or the atoms H, F, Cl, Br and I provided that $R^1$ and $R^2$ can be linked to one another via a covalent bond; each of $Q^1$ and $Q^2$ is independently selected from C, CH, $CR^3$; each of X and Z is independently selected from C, S, $CH_2$, N, P and elements of Group 4 of the Periodic Table; Y is O or OH; k is 0, 1, or 2; 1 is 0, 1, or 2; m is 1 to 3 such as 1, 2 or 3, and $R^3$ can be any of the entities (radicals, groups, or atoms) listed for $R^1$. Conveniently, each of $R^1$ and $R^2$ is independently selected from aliphatic alkoxy or aromatic alkoxy radicals, carboxyl radicals, alkoxy-carbonyl radicals and hydrocarbon radicals, each of which radicals has 1 to 20 carbon atoms.

Generally, the cyclic imide employed as the oxidation catalyst obeys the general formula (III)

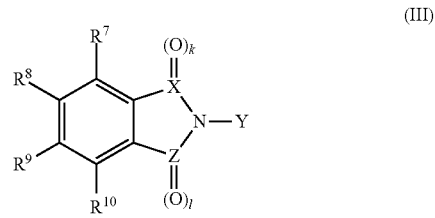

(III)

wherein each of $R^7$, $R^8$, $R^9$, and $R^{10}$ is independently selected from hydrocarbyl and substituted hydrocarbyl radicals having 1 to 20 carbon atoms, or the groups $SO_3H$, $NH_2$, OH and $NO_2$, or the atoms H, F, Cl, Br and I; each of X and Z is independently selected from C, S, $CH_2$, N, P and elements of Group 4 of the Periodic Table; Y is O or OH; k is 0, 1, or 2, and 1 is 0, 1, or 2. Conveniently, each of $R^7$, $R^8$, $R^9$, and $R^{10}$ is independently selected from aliphatic alkoxy or aromatic alkoxy radicals, carboxyl radicals, alkoxy-carbonyl radicals and hydrocarbon radicals, each of which radicals has 1 to 20 carbon atoms.

In one practical embodiment, the cyclic imide catalyst comprises N-hydroxyphthalimide.

The cyclic imide catalyst is added to the oxidation feed in an amount between about 0.05 wt % and about 5 wt %, generally between about 0.1 wt % and about 1 wt %, of the alkylaromatic in said feed. Furthermore, the cyclic imide catalyst may be added to the oxidation feed in an amount between (i) about 0.05 and about 0.10 wt %; (ii) about 0.1 wt % and about 0.2 wt %; (iii) about 0.2 wt % and about 0.3 wt %; (iv) about 0.3 wt % and about 0.4 wt %; (v) about 0.4 wt % and about 0.5 wt %; (vi) about 0.1 wt % and about 0.5 wt %, and (vii) about 0.1 wt % to 0.3 wt % of the alkylaromatic compound in said feed. Moreover, the oxidation is conducted in the substantial absence (less than 0.00001% by weight of the oxidation reaction mixture) of alkali metal compounds.

The oxidation step is conducted at relatively high temperature of between about 90° C. and about 150° C., such as between about 120° C. and about 150° C., for example between about 125° C. and about 140° C., since it is found that, with alkylaromatic compound oxidation in the presence of N-hydroxyphthalimide, the hydroperoxide selectivity against conversion reaction profile is not affected by increasing the temperature. The oxidation step is conveniently carried out at a pressure between about 15 kPa and about 500 kPa, such as between 15 kPa to about 150 kPa. By controlling the cyclic imide catalyst concentration and oxidation temperature as described herein, it is found that said alkylaromatic compound conversion rates of at least 4 wt % per hour can be achieved with a selectivity to the corresponding hydroperoxide of at least 90 wt %.

Production of Phenol

The hydroperoxide produced by the present oxidation process can be converted by acid cleavage to phenol and the corresponding ketone. The phenol can of course then be reacted with acetone to produce bisphenol A, a precursor in the production of polycarbonates and epoxy resins.

The hydroperoxide cleavage reaction is conveniently effected by contacting the hydroperoxide with a catalyst in the liquid phase at a temperature of about 20° C. to about 150° C., such as about 40° C. to about 120° C., and/or a pressure of about 50 to about 2500 kPa, such as about 100 to about 1000 kPa and/or a liquid hourly space velocity (LHSV) based on the hydroperoxide of about 0.1 to about 100 $hr^{-1}$, preferably about 1 to about 50 $hr^{-1}$. The hydroperoxide is preferably diluted in an organic solvent inert to the cleavage reaction, such as methyl ethyl ketone, cyclohexanone, phenol, sec-butylbenzene or cyclohexylbenzene, to assist in heat removal. The cleavage reaction is conveniently conducted in a catalytic distillation unit.

The catalyst employed in the cleavage step can be a homogeneous catalyst or a heterogeneous catalyst.

Suitable homogeneous cleavage catalysts include sulfuric acid, perchloric acid, phosphoric acid, hydrochloric acid and p-toluenesulfonic acid. Ferric chloride, boron trifluoride, sulfur dioxide and sulfur trioxide are also effective homogeneous cleavage catalysts. The preferred homogeneous cleavage catalyst is sulfuric acid.

A suitable heterogeneous catalyst for use in the cleavage of the hydroperoxide includes a smectite clay, such as an acidic montmorillonite silica-alumina clay, as described in U.S. Pat. No. 4,870,217 (Texaco), the entire disclosure of which is incorporated herein by reference.

The invention will now be more particularly described with reference to the following non-limiting Examples.

EXAMPLE 1

Figure 1A:
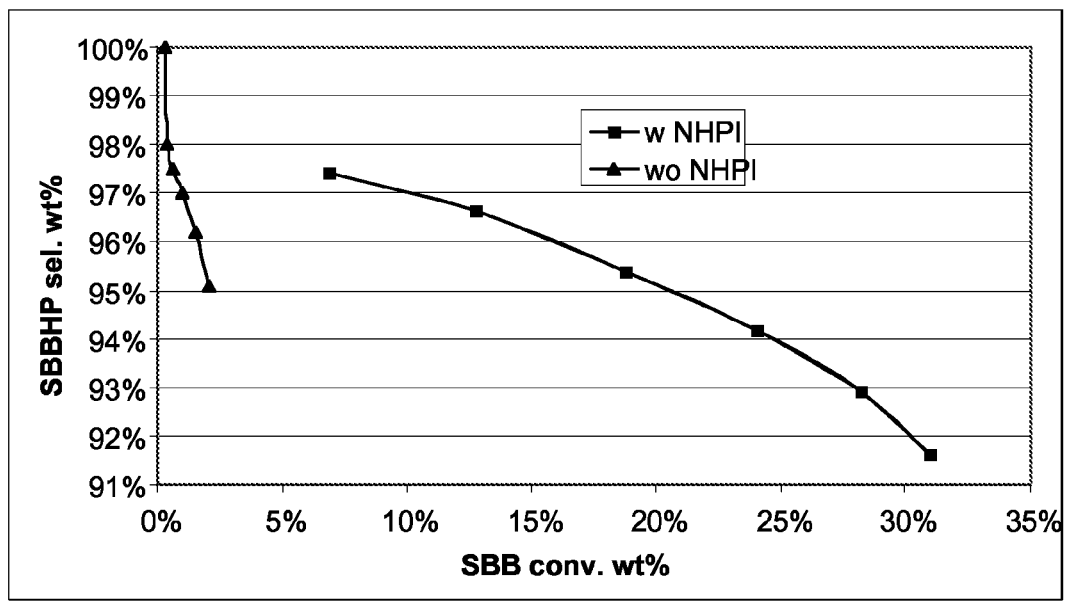
FIG. 1(a) is a graph plotting sec-butylbenzene hydroperoxide selectivity against sec-butylbenzene conversion in the oxidation of sec-butylbenzene at 115° C. without NHPI according to the process of Example 1 and in the presence of 0.43 wt % NHPI according to the process of Example 2.

SBB Oxidation without NHPI 150 gm of sec-butylbenzene (SBB) supplied by TCI America was weighed into a 300 ml Parr reactor fitted with a stirrer, thermocouple, gas inlet, sampling port and a condenser containing a Dean Stark trap for water removal. The reactor and contents were stirred at 700 rpm and sparged with nitrogen at a flow rate of 250 cc/minute for 5 minutes. The reactor was then pressurized with nitrogen to 690 kPag (100 psig) while maintained under a nitrogen sparge and was then heated to 115° C. When the reaction temperature was reached, the gas was switched from nitrogen to air and the reactor was sparged with air at 250 cc/minute for 6 hours. Samples were taken hourly and analyzed by gas chromatography. After 6 hours, the gas was switched back to nitrogen and the heat was turned off. When the reactor had cooled, it was depressurized and the contents removed. The conversion results are shown in FIG. 1, and the selectivity results plotted against the conversion results are shown in FIG. 1(a).

EXAMPLE 2

SBB Oxidation in the Presence of NHPI

The process of Example 1 was repeated but with 0.64 gm (0.43 wt %) of N-hydroxyphthalimide (NHPI) being weighed into the Parr reactor with the 150 gm of sec-butylbenzene (SBB). Again the conversion results are shown in FIG. 1, and the selectivity results are shown in FIG. 1(a), from which it will be seen that addition of the NHPI dramatically improved the SBB conversion level. The addition of the NHPI also improved the selectivity to sec-butylbenzene hydroperoxide (SBBHP) based on equivalent conversion levels.

EXAMPLE 3

SBB Oxidation at Different Levels of NHPI

Figure 2:
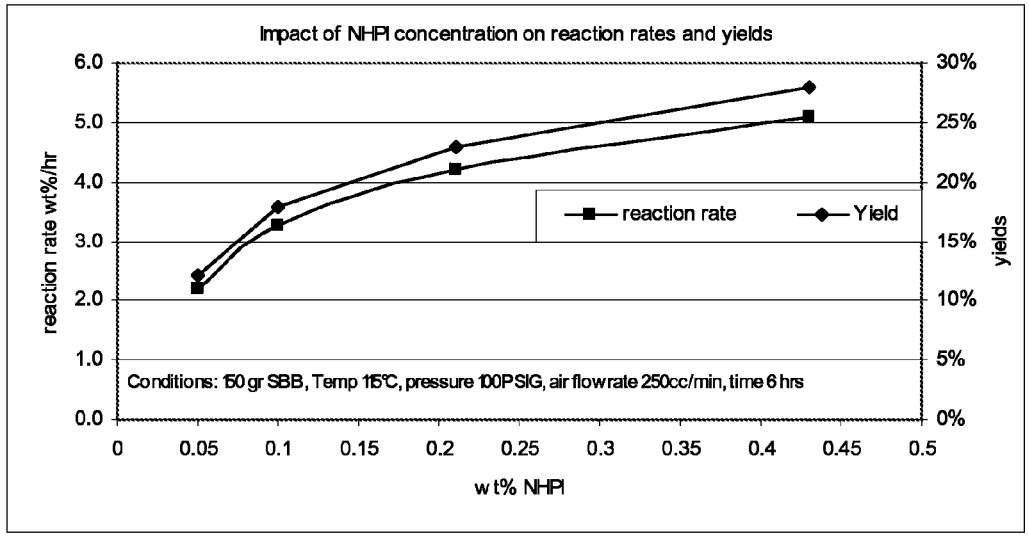
FIG. 2 is a graph plotting reaction rate and sec-butylbenzene hydroperoxide yield against NHPI concentration in the oxidation of sec-butylbenzene at 115° C. with varying amounts of NHPI according to the process of Example 3.
Figure 3:
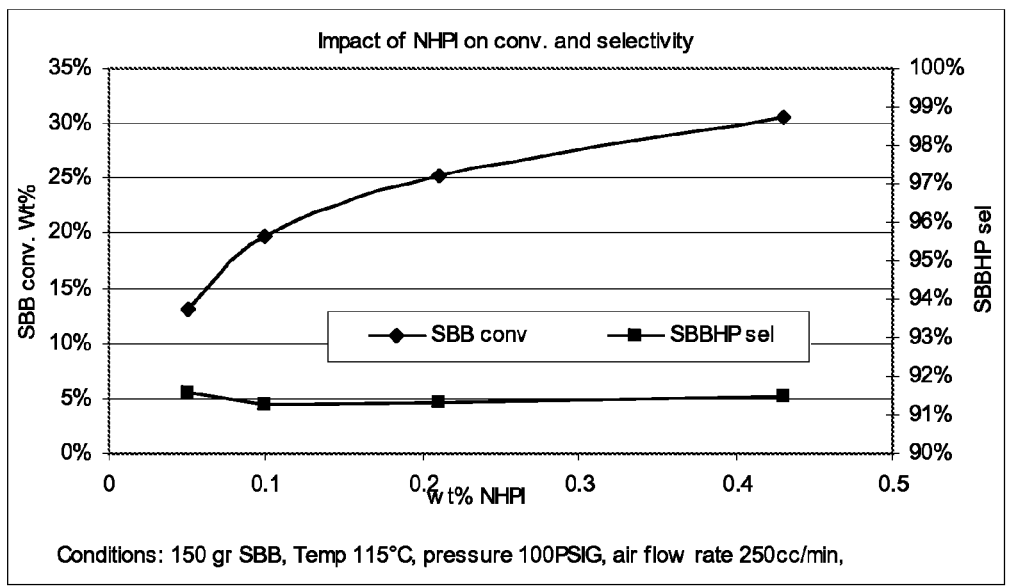
FIG. 3 is a graph plotting sec-butylbenzene conversion and sec-butylbenzene hydroperoxide selectivity against NHPI concentration in the oxidation of sec-butylbenzene at 115° C. with varying amounts of NHPI according to the process of Example 3.

The procedure of Example 2 was repeated with the addition of different amounts of NHPI, namely 0.05, 0.125, 0.215 and 0.43 wt %. The results are plotted in FIGS. 2 and 3 and show the impact of NHPI concentration on reaction rate and sec-butylbenzene hydroperoxide yield (the product of SBB conversion and SBBHP selectivity). The data show that the selectivity to the SBB hydroperoxide is flat at different yields and NHPI content.

EXAMPLE 4

SBB Oxidation at Different NHPI Concentrations and Temperature of 125° C.

Figure 4:
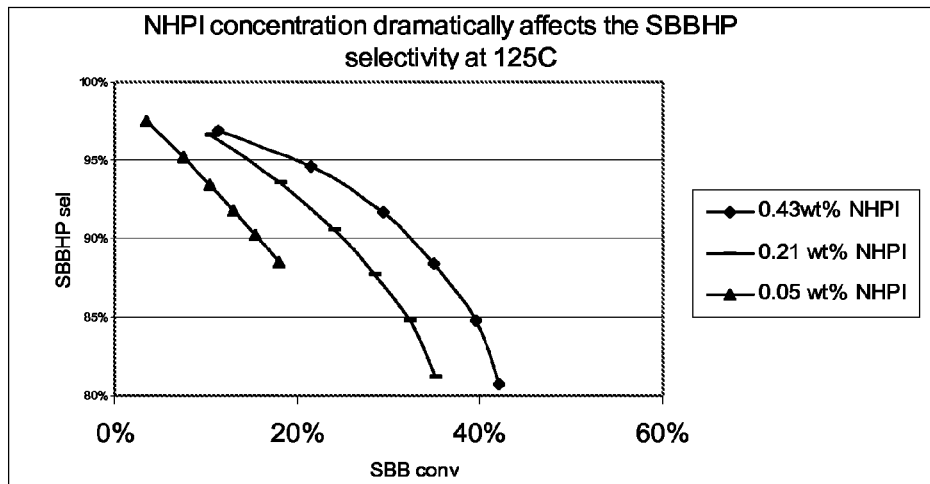
FIG. 4 is a graph plotting sec-butylbenzene hydroperoxide selectivity against sec-butylbenzene conversion in the oxidation of sec-butylbenzene at 125° C. with varying amounts of NHPI according to the process of Example 4.

The procedure of Example 3 was repeated with the addition of NHPI in amounts of 0.05, 0.215 and 0.43 wt % and with the reaction temperature increased to 125° C. The results are plotted in FIG. 4 and show that at 125° C. the hydroperoxide selectivity and the SBB conversion are significantly affected by increasing the NHPI concentration. At higher NHPI concentration, higher selectivities are achieved at the same conversion level.

EXAMPLE 5

SBB Oxidation at Different Temperature and NHPI Concentrations of 0.05 and 0.10 wt %

Figure 5A:
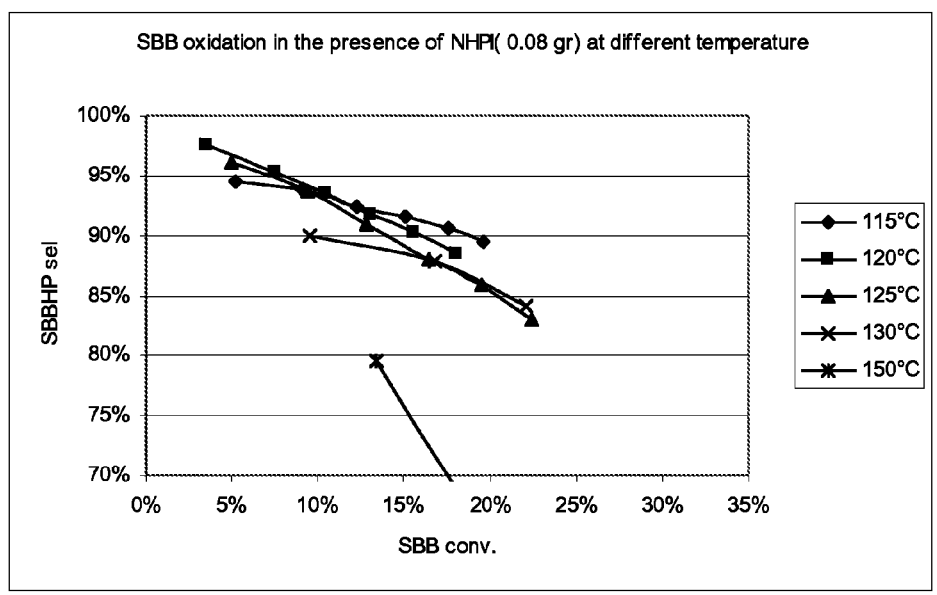
FIGS. 5(a) and (b) are graphs plotting sec-butylbenzene hydroperoxide selectivity against sec-butylbenzene conversion in the oxidation of sec-butylbenzene at varying temperatures between 115° C. and 150° C. in the presence of 0.05 wt % NHPI [FIG. 5(a)] and 0.10 wt % NHPI [FIG. 5(b)] according to the process of Example 5.
Figure 5B:
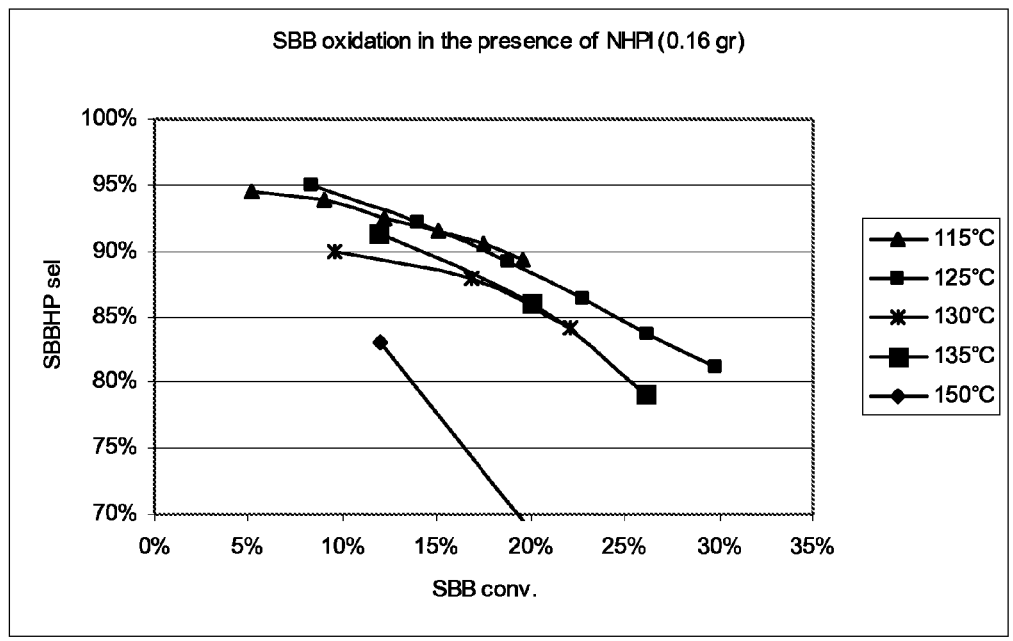
Figure 6A:
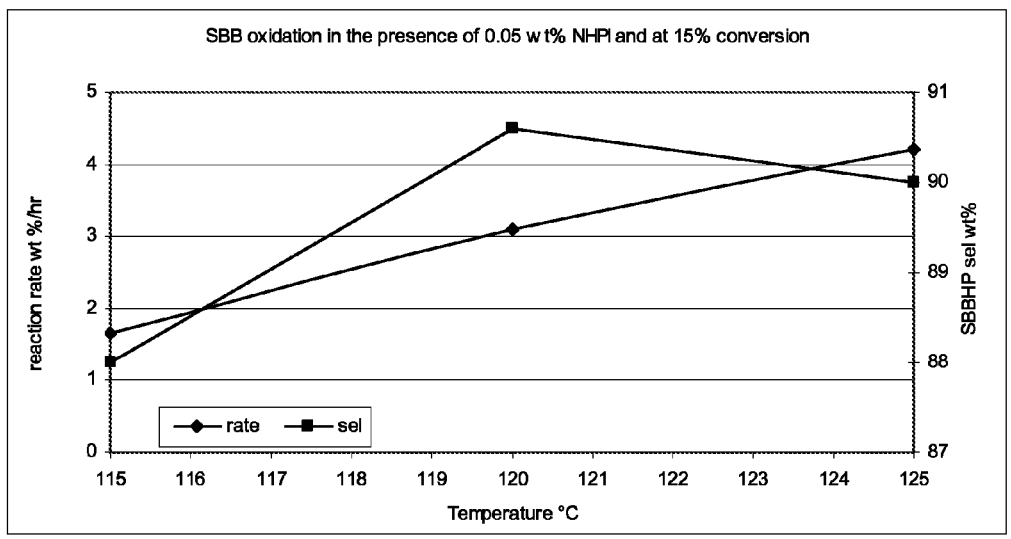
FIGS. 6(a) and (b) are graphs plotting reaction rate and sec-butylbenzene hydroperoxide selectivity against temperature in the oxidation of sec-butylbenzene in the presence of 0.05 wt % NHPI [FIG. 6(a)] and 0.10 wt % NHPI [FIG. 6(b)] according to the process of Example 5.
Figure 6B:
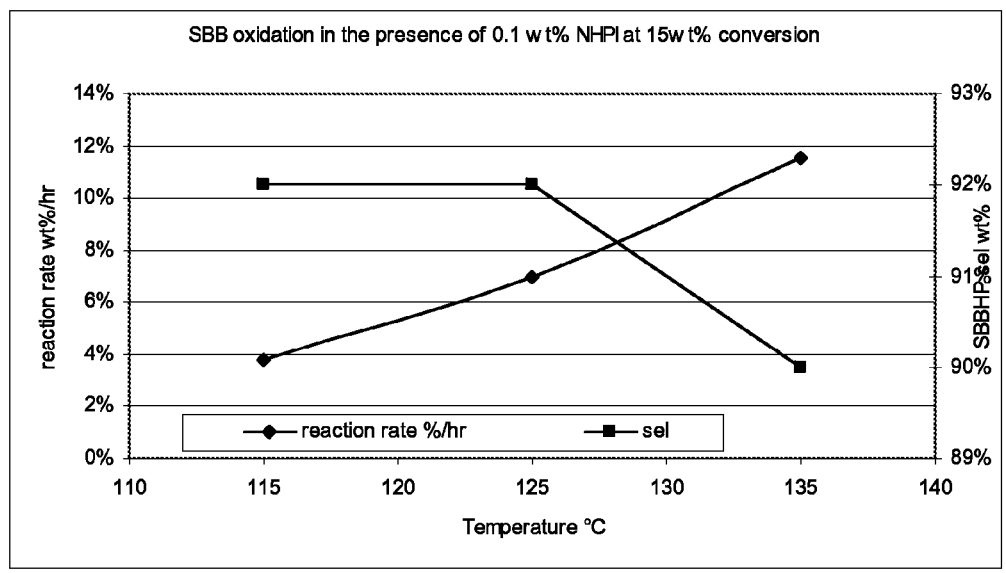

The procedure of Example 3 was repeated with the addition of NHPI in amounts of 0.05 and 0.10 wt % and with the reaction temperature being varied between 115° C. and 150° C. The results are plotted in FIGS. 5 and 6 and show at these NHPI concentrations varying the temperature between 115 and 125° C. has no impact on the selectivity against conversion profile.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A process for oxidizing an alkylaromatic compound to the corresponding alkylaromatic hydroperoxide, the process comprising contacting an alkylaromatic compound of general formula (I):

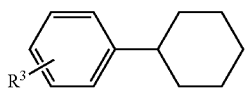
(I)

in which R³ represents hydrogen, one or more alkyl groups having from 1 to 4 carbon atoms or a cyclohexyl group, with air in the presence of a catalyst comprising a cyclic imide of the general formula (II):

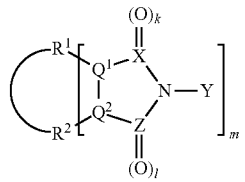
(II)

wherein each of R¹ and R² is independently selected from hydrocarbyl and substituted hydrocarbyl radicals having 1 to 20 carbon atoms, or from the groups SO₃H, NH₂, OH, and NO₂ or from the atoms H, F, Cl, Br, and I, provided that R¹ and R² can be linked to one another via a covalent bond;
each of Q¹ and Q² is independently selected from C, CH, CR³;
each of X and Z is independently selected from C, S, CH₂, N, P and elements of Group 4 of the Periodic Table;
Y is O or OH;
k is 0, 1, or 2;
l is 0, 1, or 2;
m is 1 to 3; and
R³ can be any of the entities listed for R¹; and
wherein said contacting is conducted at a temperature of about 90° C. to about 150° C. and a pressure of between about 15 kPa and about 500 kPa, said cyclic imide is present in an amount between about 0.05 wt % and about 5 wt % of the alkylaromatic compound in said feed, and said catalyst is substantially free of alkali metal compounds, said contacting oxidizing at least part of the alkylaromatic compound in said feed to the corresponding alkylaromatic hydroperoxide.

2. The process of claim 1, wherein said cyclic imide obeys the general formula (II):

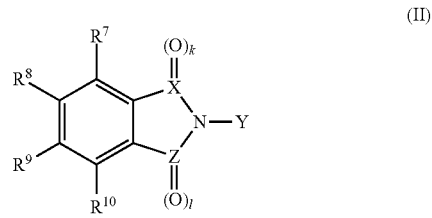
(II)

wherein each of R⁷, R⁸, R⁹, and R¹⁰ is independently selected from hydrocarbyl and substituted hydrocarbyl radicals having 1 to 20 carbon atoms, or from the groups SO₃H, NH₂, OH, and NO₂ or from the atoms H, F, Cl, Br, and I,
each of X and Z is independently selected from C, S, CH₂, N, P and elements of Group 4 of the Periodic Table;
Y is O or OH,
k is 0, 1, or 2, and
l is 0, 1, or 2.

3. The process of claim 1, wherein said cyclic imide comprises N-hydroxyphthalimide.

4. The process of claim 1, wherein said contacting is conducted at a temperature of between about 125° C. and about 140° C. and a pressure of about 15 kPa to about 150 kPa.

5. The process of claim 1, wherein said cyclic imide is present in an amount between about 0.1 wt % and about 1 wt % of the alkylaromatic in said feed during said contacting.

6. The process of claim 1, wherein said cyclic imide is present in an amount between about 0.05 wt % and about 0.5 wt % of the alkylaromatic in said feed during said contacting.

7. The process of claim 1, wherein said contacting converts at least 4 wt % per hour conversion of said alkylaromatic compound with a selectivity to the corresponding alkylaromatic hydroperoxide of at least 90 wt %.

8. The process of claim 1, wherein said alkylaromatic compound is cyclohexylbenzene.

9. The process of claim 1, further comprising the step of:
cleaving the alkylaromatic hydroperoxide to produce phenol and the corresponding ketone.

10. The process of claim 9, wherein the cleaving is conducted in the presence of a catalyst.

11. The process of claim 9, wherein the cleaving is conducted in the presence of a homogeneous catalyst.

12. The process of claim 11, wherein said homogeneous catalyst comprises at least one of sulfuric acid, perchloric acid, phosphoric acid, hydrochloric acid, p-toluenesulfonic acid, ferric chloride, boron trifluoride, sulfur dioxide and sulfur trioxide.

13. The process of claim 9, wherein the cleaving is conducted in the presence of a heterogeneous catalyst.

14. The process of claim 13, wherein said heterogeneous catalyst comprises a smectite clay.

15. The process of claim 9, wherein the cleaving is conducted at a temperature of about 40° C. to about 120° C., a pressure of about 100 to about 1000 kPa, and a liquid hourly space velocity (LHSV) based on the hydroperoxide of about 1 to about 50 hr⁻¹.

16. The process of claim 1, wherein the air is subjected to water removal.

* * * * *